United States Patent [19]

Tustin et al.

[11] Patent Number: 5,138,108
[45] Date of Patent: Aug. 11, 1992

[54] PROCESS FOR REGENERATING A ZEOLITE CATALYST

[75] Inventors: Gerald C. Tustin; Joseph F. Jeter; Richard I. Garrity, all of Kingsport, Tenn.

[73] Assignee: Eastman Kodak Company, Rochester, N.Y.

[21] Appl. No.: 776,018

[22] Filed: Oct. 15, 1991

Related U.S. Application Data

[63] Continuation-in-part of Ser. No. 620,812, Dec. 3, 1990, abandoned.

[51] Int. Cl.$^5$ ............................................. C07C 11/152
[52] U.S. Cl. ..................................... 570/203; 570/206
[58] Field of Search ................................. 570/203, 206

[56] References Cited

U.S. PATENT DOCUMENTS

| | | |
|---|---|---|
| 3,493,490 | 2/1970 | Plank et al. . |
| 3,533,959 | 10/1970 | Miale et al. . |
| 4,468,475 | 8/1984 | Kuehl . |
| 4,678,763 | 7/1987 | Chang et al. . |
| 4,746,758 | 5/1988 | Rule et al. . |
| 4,778,356 | 10/1988 | Hicks . |
| 4,778,938 | 10/1988 | Rule et al. . |
| 4,778,939 | 10/1988 | Tustin et al. . |
| 4,778,940 | 10/1988 | Rule et al. . |
| 4,792,641 | 12/1988 | Rule et al. . |
| 4,792,642 | 12/1988 | Rule et al. . |
| 4,806,697 | 2/1989 | Rule et al. . |
| 4,853,480 | 8/1989 | Tustin et al. . |

OTHER PUBLICATIONS

Klinowski et al. in Applied Catalysis, 56, L15 (1989).

*Primary Examiner*—Howard T. Mars
*Assistant Examiner*—Kimberly J. Kestler
*Attorney, Agent, or Firm*—Charles R. Martin; William P. Heath, Jr.

[57] ABSTRACT

Disclosed is a process for regeneration of a 13X zeolite catalyst comprising conducting the following steps within the regeneration zone wherein the 13X zeolite is located.

(1) Applying vacuum or delivering a source of molecular oxygen or inert gas at a temperature above 100° C. to remove a portion of the volatile compounds from the 13X zeolite,
(2) Cooling the 13X zeolite to a temperature below 100 degrees C.,
(3) Contacting the 13X zeolite with an aqueous solution having a pH in the range of 7 to 14,
(4) Drying the 13X zeolite,
(5) Delivering an oxygen containing calcination gas to the regeneration zone and heating the 13X zeolite to a temperature in the range of 350° to 450° C.,
(6) Cooling the 13X zeolite to a temperature below 100 degrees C., and
(7) Contacting the 13X zeolite with an aqueous solution having a pH in the range of 7 to 14.

3 Claims, No Drawings

PROCESS FOR REGENERATING A ZEOLITE CATALYST

This application is a continuation in part of Ser. No. 07/620,812, filed Dec. 3, 1990, now abandoned.

This invention relates to the regeneration of a zeolite catalyst used for the oxyiodination of aromatic compounds.

It has long been desired to be able to derivatize aromatic compounds and in particular condensed ring aromatic compounds in commercially attractive quantities since many of these compounds possess properties which would fill long sought needs. In particular, the compound 2,6-naphthalenedicarboxylic acid or its esters is particularly desired for use in the manufacture of polyesters which have excellent barrier properties when fabricate into films, bottles or coatings.

One of the most effective means to prepare an aromatic dicarboxylic acid such as 2,6-naphthalenedicarboxylic acid or terephthalic acid is to carboxylate 2,6-diiodonaphthalene or 1,4-diiodobenzene produced by reacting naphthalene or benzene with iodine and an oxygen source in the presence of a zeolite catalyst as disclosed in U.S. Pat. No. 4,778,938 and U.S. Pat. No. 4,746,758. Although the process disclosed in these patents is very desirable, the activity of the catalyst diminishes after prolonged operation of the process.

Although processes for regeneration of certain kinds of zeolite catalysts are known in the art, the prior art does not disclose a process to regenerate zeolite 13X in the alkali metal exchanged form.

U.S. Pat. No. 3,493,490 describes the regeneration of heat or steam damaged zeolites which do not contain an alkali metal ion by a hydrothermal treatment with liquid water. This technique is not suitable for the regeneration of the zeolite catalyst useful in the above described oxyiodination of aromatic compounds because this technique is limited to a zeolite which does not contain an alkali metal ion and the zeolites useful in the above described oxyiodination process incorporate an alkali metal ion.

U.S. Pat. No. 3,533,959 describes the use of a chelating agent at a pH between 7 and 9 to reclaim damaged large pore zeolite cracking catalysts. This technique is not suitable for the zeolites useful in the above described oxyiodination process because the action of a chelating agent on zeolite X causes dealumination to occur which leads to loss of crystallinity.

U.S. Pat. No. 4,468,475 and U.S. Pat. No. 4,678,763 describe hydrothermal treatments of high silica to alumina zeolites. As disclosed in Klinowski et al in Applied Catalysis, 56, L15 (1989), this technique is only applicable to zeolites with Si/Al ratios of about 25 or higher. This technology is not suitable for the zeolites useful in the above described oxyiodination process because these zeolites have ratios of Si/Al of less than 3.

In view of the above prior art a need exists for a method that will repair damaged zeolite 13X in the alkali metal exchanged form.

A further need exists for a method that will remove coke deposits from fouled zeolite 13X in the alkali metal exchanged form without extensively and irreversibly damaging the crystal structure of the zeolite.

Still a further need exists for a method that will restore the activity of a deactivated zeolite 13X oxyiodination catalyst containing potassium, rubidium, or cesium ions to a level similar to that of a fresh catalyst in such a manner that the subsequent rate of deactivation resulting from oxyiodination conditions is similar to that of a fresh catalyst and in such a manner that the selectivity of the regenerated catalyst is similar to that of a fresh catalyst We have now discovered a process that not only restores the activity of a deactivated zeolite 13X oxyiodination catalyst containing an alkali metal ion to a level similar to that of a fresh catalyst but also restores the zeolite in the sense that the subsequent rate of deactivation resulting from oxyiodination conditions is similar to that of a fresh catalyst and the selectivity of the regenerated catalyst is similar to that of a fresh catalyst.

In summary, this process involves regenerating the zeolite by the following steps.

(1) Applying vacuum or delivering a source of molecular oxygen or inert gas at a temperature above 100° C. to the regeneration zone to remove a portion of the volatile compounds from the zeolite.

(2) Cooling the zeolite in the regeneration zone to a temperature below 100° C.

(3) Contacting the zeolite in the regeneration zone with an aqueous solution having a pH in the range of 7 to 14.

(4) Drying the zeolite in the regeneration zone.

(5) Delivering an oxygen containing calcination gas to the regeneration zone and heating the zeolite in the regeneration zone to a temperature in the range of 350° to 450° C.

(6) Cooling the zeolite in the regeneration zone to a temperature below 100° C.

(7) Contacting the zeolite in the regeneration the range of 7 to 14.

The process of this invention is particularly applicable to regenerating a 13X zeolite used in the oxyiodination of naphthalene or benzene. The oxyiodination of naphthalene or benzene is accomplished by reacting within a reaction zone naphthalene or benzene and a source of molecular oxygen in the presence of a 13X zeolite which has a pore size of at least 6 angstroms and preferably has greater than 10% of the exchangeable cations as alkali, alkaline earth or rare earth metals. Details concerning this process are well known in the art and are described in U.S. Pat. No. 4,746,758, U.S. Pat. No. 4,778,938, U.S. Pat. No. 4,778,939, U.S. Pat. No. 4,778,940 or U.S. Pat. No. 4,792,642, herein incorporated by reference. An iodine generator as described in U.S. Pat. No. 4,853,480 and product separation schemes as described in U.S. Pat. No. 4,778,356 may be incorporated into the oxyiodination processes for which the regeneration scheme is applicable. Catalysts deactivated by the transiodination/isomerization reactions described in U.S. Pat. No. 4,792,641 and U.S. Pat. No. 4,806,697 may also be regenerated by the process of this invention.

Obviously there is no need to utilize the process of this invention until the activity of the zeolite is diminished; however, it is important that the regeneration process of this invention be performed before catastrophic deactivation of the zeolite occurs. The reduction in activity of a zeolite catalyst typically occurs in three stages. Initially there is a rapid drop in activity which is followed by a very gradual drop in activity and finally by an substantially accelerated drop in activity. The final substantial accelerated drop in activity is the catastrophic deactivation stage. The length of time between the start of the oxyiodination reaction and the occurrence of catastrophic deactivation depends on many reaction parameters such as the identity of the aromatic compound, the space velocities of the aromatic compound, iodine and oxygen containing gas, the reaction temperature and the nature and amount of any impurities. Thus, the length of time between the start of the oxyiodination reaction and the occurrence of catastrophic deactivation must be determined experimentally for each reaction system of interest. Generally oxyiodination reaction times between 6 and 3000 hours are possible before catastrophic deactivation occurs. More typical reaction times before the occurrence of catastrophic deactivation are between 24 and 2000 hours with 50 to 200 hours being most typical. Although some activity can be regained if the regeneration procedure is performed after the onset of catastrophic deactivation typically the regeneration process would be performed prior to catastrophic deactivation.

According to this invention the zeolite catalyst can be regenerated in place in the oxyiodination reactor or it can be removed from the oxyiodination reactor and regenerated in another location. In a preferred embodiment the catalyst is allowed to remain in the oxyiodination reactor and the catalyst is regenerated within the oxyiodination reactor.

The first step of the regeneration process is delivering a source of molecular oxygen or inert gas at a temperature above 100° C. to the regeneration zone to remove a portion of the volatile compounds from the zeolite. A vacuum may be applied to the reaction zone in lieu of oxygen or inert gas. In a preferred embodiment the gaseous source of molecular oxygen used for the oxyiodination reaction can be used. The length of time after the cessation of the oxyiodination reaction that the source of molecular oxygen or inert gas is fed over the catalyst is not critical and depends on many factors including the nature of the aromatic compounds and level of iodine originally fed, the reaction temperature, and the rate of flow of the oxygen containing gas. Generally the treatment to remove volatile compounds is continued until no additional material condenses when the off gas is cooled to 20°-30° C. Typical times for the removal of volatile materials from the catalyst range from 5 minutes to 2 days with shorter or longer times being possible. It is desirable that the adhering materials be removed from the catalyst so as to allow the aqueous solutions to wet the catalyst and to minimize excessive exotherms in the subsequent calcination. Therefore, in an optional embodiment, the catalyst can be washed with a volatile solvent to dissolve material adhering to the zeolite and then the volatile solvent removed.

In the second step the zeolite is cooled to a temperature below 100° C. It is more preferable to cool the catalyst to a temperature near ambient temperature or to about 20°-30° C. If the catalyst is moisture free it may be optionally desirable to slowly hydrate the catalyst by passing an air or inert gas stream saturated with water vapor over the catalyst until the catalyst is saturated with water. This prevents excess shock to the catalyst occurring as result of it being contacted with the aqueous solution in a dry state. Hydration of the catalyst is continued until about 30 wt % of the initial catalyst weight in water has been passed over the catalyst. The rate of hydration of the catalyst should be controlled to prevent excessive rises in temperature with maximum hydration temperatures generally being less than 100 degrees C.

In the third step the catalyst is contacted with an aqueous solution. The pH of the aqueous solution is between 7 and 14, preferably between 9 and 14 and most preferably between 11 and 13.2. The pH of the solution may be adjusted by the addition of base or by the natural hydrolysis of the cations in the zeolite which occurs when the zeolite is brought into contact with water. When base is added, it is preferable that the cation of the base be the same as the cation in the zeolite. The anion of the base may be hydroxide, carbonate, bicarbonate, alkoxide or carboxylate or the like. Thus, when the potassium form of the 13X zeolite is used, the preferred base is potassium hydroxide. If the zeolite is zeolite 13 X exchanged with potassium, the volume of aqueous solution contacted with the zeolite catalyst is generally between 1 and 100 ml per gram of catalyst with values between 5 and 50 ml per gram of catalyst being preferred. The temperature of the aqueous solution may range from about zero degrees C to 100° C. or greater. The preferred temperatures range from about 20° C. to about 80° C. The duration of the hydrothermal treatment can range from about 5 minutes to 48 hours or longer. Preferred durations range from 2 to 24 hours. The mixture of zeolite and aqueous solution may be maintained in an essentially static mode if the catalyst is regenerated in place or may be stirred if the catalyst is removed from the oxyiodination reactor and regenerated in other equipment. If the mixture is stirred, care should be taken to avoid abrasion of the zeolite if it is in a composite form. Although the aqueous solution can be contacted with the zeolite by various means well known in the art, in a preferred embodiment the catalyst is regenerated in place in the oxyiodination reactor and the aqueous solution is circulated through the zeolite catalyst by means of a pump. After the completion of the contacting step the aqueous solution is removed from the zeolite catalyst by decantation or filtration. Optionally, additional washing of the zeolite catalyst with water or an aqueous solution containing base may be accomplished. The temperature and volume of the wash solution are not critical provided they are similar to the aqueous solution. The duration of the wash step can be conducted until no further pH change is observed on continued washes. The washing solution can be removed from the zeolite catalyst by decantation or filtration.

The zeolite catalyst at this stage of the regeneration is wet and the fourth step is to dry the catalyst. It is preferable that the catalyst be dried at a low temperature. A convenient way to accomplish the drying step is to pass the same gas mixture that is used in the fifth step over the catalyst at 80° to 120° C. until the water content of the off gas is approximately equal to that of the ambient atmosphere. Other drying methods, such as vacuum drying can be used provided they do not damage the catalyst.

After drying is completed, the fifth step is calcination of the zeolite by delivering an oxygen containing calcination gas to the regeneration zone while heating the zeolite to a temperature in the range of 350° to 450° C. The calcination gas is passed over the catalyst while the temperature is slowly elevated. The calcining gas can comprise any oxygen containing gas that is useful to the practice of this invention. The percent molecular oxygen in the calcination gas should be selected so that excessive exotherms are not produced in the calcination process. The amount of molecular oxygen in the calcination gas can vary depending on the coke content of the catalyst, the space velocity and the rate of planned temperature increase. Preferably the calcination gas is air and more preferably the air is diluted with an inert gas such as nitrogen. In general, oxygen levels on the order of 1 to 2% by volume have proven satisfactory. It is desirable to maintain a minimum level of water vapor in the calcination gas and passing the gas over the zeolite catalyst at high space velocity can help in attaining this goal. In general, gas flow rates of about 3 liters per kilogram of catalyst per minute at standard temperature and pressure have proven satisfactory. Higher or lower flow rates can be used depending on the amount of coke present, the amount of oxygen in the gas and whether the temperature where coke combustion begins has been reached. The rate of temperature increase should be selected to prevent excessive exotherms and uncontrolled water evolution which can cause stream degradation of the zeolite catalyst. Typically after the preliminary drying is completed the temperature can be increased to about 200° C. During this part of the process most of the visible water evolution occurs. When larger amounts of catalyst are regenerated it is preferable to hold the temperature at 200° C. until the visible evolution of water has ceased. After the visible evolution of water has ceased, the temperature is elevated above 350° C., preferably above 400° C. The rate of temperature increase should be chosen to avoid excessive exotherms. The temperature of the catalyst should not be significantly above 450° C. A rate of temperature increase of 50° per hour is typical. The temperature can be further increased to about 450° C. if necessary to accomplish the final removal of the coke deposits with care taken to avoid exotherms that take the bed temperature significantly above 450° C. The temperature can be maintained at this point until the removal of the coke deposit is complete, and the oxygen level can be increased at this point to increase the rate of coke removal provided care is taken to avoid exotherms significantly above 450° C. The upper limit of the calcination temperature is between about 350° and 500° C with 400° to 450° C. being the preferred region. Since extended periods at high temperature can be detrimental to the zeolite catalyst, it is desirable to optimize each case individually to allow for the shortest time possible at elevated temperature. However calcination times of two days or longer at 450° C. are possible without excessive catalyst damage.

The sixth step is to cool the catalyst to below 100° C. It is more preferable to cool the catalyst to a temperature near ambient temperature or to about 20°–30° C. It may be optionally desirable to slowly hydrate the catalyst by passing an air or inert gas stream saturated with water vapor over the catalyst until the catalyst is saturated with water. This presents excess shock to the catalyst from occurring when it is contacted with the aqueous solution when it is in a dry state. The vapor hydration of the catalyst can be continued until about 30 wt % of the initial catalyst weight in water has been passed over the catalyst. The rate of hydration of the catalyst should be controlled to prevent excessive rises in temperature with the maximum hydration temperatures generally being less than 100° C. The desirability of the slow vapor hydration step becomes greater as the amount of catalyst and degree of confinement become greater. Generally this step is not required when the catalyst charge in a packed reactor is on the order of 100-200 grams or less.

In the seventh step of the regeneration process the catalyst is contacted with an aqueous solution. This step is performed identically to step three.

At the conclusion of the regeneration process the catalyst is wet and should be dried before the oxyiodination reaction is resumed. A convenient way to accomplish drying is to pass air or an inert gas over the catalyst at 80° to 120° C. until the water content of the off gas is approximately equal to that of the ambient atmosphere. Other drying methods, such as vacuum drying, can be used provided they do not damage the catalyst. After the drying step is completed the oxyiodination reaction can be resumed.

The regeneration process can be performed as a batch or as a continuous process. When batch regeneration is performed it may be desirable to remove the catalyst from the oxyiodination reactor and perform the regeneration in separate equipment. Alternatively it may be desirable to perform all of the regeneration steps in the oxyiodination reactor, and, in this case, several reactors may be used with various stages of regeneration being performed in some reactors while oxyiodination reactions are being performed in others. When a totally continuous mode of regeneration/oxyiodination is desired, moving or fluidized bed techniques can be used.

The following examples are presented to illustrate the present invention, but are not intended in any way to limit the scope of the invention which is defined by the appended claims.

Examples 1-6 illustrate the regeneration of the catalyst on an exact catalyst weight basis with variability established by triplicate oxyiodination reactions on fresh catalyst (Example 1-3) and duplicate oxyiodination reactions (Example 5 and 6) on catalyst regenerated by the method of the invention (Example 4). The same starting catalyst was used in all of the examples and was a 92% potassium exchanged form of zeolite 13X beads of 16×40 mesh size containing 20 weight % clay binder. Products were identified by gas chromatography.

EXAMPLE 1

A one inch O.D. quartz tubular reactor fitted with an internal thermocouple well was loaded with a support bed of coarse quartz chips to position the catalyst near the center of the tube, a thin layer of quartz wool, 4.17 grams of the zeolite catalyst, a second thin layer of quartz wool and finally with a second bed of quartz chips used to preheat and insure mixing of the reactants as they enter the top of the reactor. The reactor was placed in an electric furnace and heated to 250° C. in the presence of 400 standard cubic centimeters per minute of air. After the catalyst temperature had stabilized at 250° C., naphthalene was added at a rate of 3.0 mmol/min and an additional 116 standard cubic centimeters per minute of air was also added. The heat of adsorption of naphthalene causes a small exotherm to occur, and, after the catalyst bed temperature returned to 250° C., iodine was added at a rate of 0.6 mmol/min and an additional 69 standard cubic centimeters per minute of air was also added. This point of the reaction was considered to be start of the reaction (time=0). The reaction was allowed to continue for one hour, and a tared vented sample bottle held at ambient room temperature was placed at the base of the reactor. The product was collected for a period of one hour, then the bottle was removed, weighted, and the products analyzed by gas chromatography. Similar samples were collected between hours 5 and 6 of the reaction and between hours 23 and 24 of the reaction. The identity and the weight percentages of each component are shown in Table 1.

After the 24 hours sample had been collected, the iodine feed was stopped, and the naphthalene and 516 standard cubic centimeters per minute air were fed over the catalyst for an additional hour at 250° C. The naphthalene feed was then stopped, the air feed was continued at 250° C. and 400 standard cubic centimeters per minute until no additional condensation was visible at the base of the reactor, and then the reactor was allowed to cool under a feed of 400 standard cubic centimeters per minute of air. After the reactor had cooled to room temperature, the air feed was stopped, and the reactor was removed from the furnace. The quartz chips from the preheat/mixing zone were removed by inverting the reactor. The upper layer of quartz wool was removed from the reactor by hooking the quartz wool with a wire hook and carefully pulling it out of the reactor. The catalyst was collected at this point by pouring it out of the reactor.

EXAMPLE 2

In order to establish the range of variability among identical runs and provide sample for the regeneration process, the process of Example 1 was repeated. The identity and the weight percentages of each component are shown in Table 1.

EXAMPLE 3

In order further establish the range of variability among identical runs and provide sample for the regeneration process, the process of Examples 1 and 2 was repeated. The identify and weight percentages of each component are shown in Table 1. Also shown in Table 1 are the averages of the weight percentages from Examples 1-3.

EXAMPLE 4

This example illustrates the regeneration process of the invention. The used catalyst charges recovered from Examples 1, 2 and 3 were combined. The catalyst was transferred to a 1 liter polypropylene bottle, and aqueous potassium hydroxide solution (577 ml) of pH 13 was added, the bottle was capped, and the entire mixture was placed in an oven held at 80°. The mixture was heated in the oven for 24 hours and was swirled three times for about thirty seconds each time during the hydrothermal treatment. The mixture was then removed from the oven and decanted. The catalyst was then washed with an aqueous potassium hydroxide solution (100 ml) of pH 9 at room temperature for a period of 15 minutes. The wash solution was then decanted. The washing and decanting procedures were repeated six more times. The catalyst was then dried in an oven at 125° for an hour and then at 150° overnight. The catalyst was then returned to a one inch O.D. quartz tubular reactor fitted with an internal thermocouple well, a support bed of coarse quartz chips and a thin layer of quartz wool. The reactor was placed in an electric furnace with the catalyst positioned in the middle of the furnace. Nitrogen (124 standard cubic centimeters per minute) and air (25 standard cubic centimeters per minute) were fed to the reactor, and the furnace was set for 250° C. Heating was continued for one hour at 250° C., and the temperature was raised to 300° C. and held at 300° C. overnight. The temperature was then raised to 350° C., held at 350° C. for 2 hours, raised to 400° C. and held at 400° C. for 4 hours. The nitrogen feed was stopped, and the temperature was increased to 450° C. and held at 450° C. overnight. The catalyst was allowed to cool to room temperature under the flow of air. The catalyst was placed into a 1 liter polypropylene bottle, and an aqueous potassium hydroxide solution (600 ml) of pH 13 was added. The bottle was capped, and the entire mixture was placed into an oven held at 80° C. The mixture was heated in the oven for 24 hours and was swirled occasionally for about thirty seconds each time during the hydrothermal treatment. The mixture was removed from the oven and decanted. The catalyst was washed with distilled water (100 ml) at room temperature for 15 minutes and decanted. The washing and decanting procedure was repeated six more times. The pH of the final decanted solution was 9. Sufficient catalyst was recovered to allow for two more oxyiodination reactions to be evaluated using an identical mass (4.17) of regenerated catalyst to that of the fresh catalyst used in Examples 1-3. These are provided in Examples 5 and 6.

EXAMPLE 5

A 4.17 gram charge of the regenerated catalyst of Example 4 was subjected to the oxyiodination conditions of Example 1. The identity and weight percentages of each component are shown in Table 2.

EXAMPLE 6

In order to establish the range of variability between identical runs, the process of Example 5 was repeated. The identity and weight percentages of each component are shown in Table 2. Also shown in Table 2 are the averages of the weight percentages from Examples 5 and 6. Comparison of the data in Table 1 with that in Table 2 indicates that the performance of the regenerated catalyst is identical or even slightly superior to that observed with the fresh catalyst within the range of variability of the experiments. The differences in the average weight percentage values between the regenerated (average of Examples 5-6) and fresh (average of Examples 1-3) catalysts are summarized in Table 3.

TABLE 1

| PERFORMANCE OF FRESH CATALYST | | | | | | |
|---|---|---|---|---|---|---|
| EXAMPLE NO. | 1 | | | 2 | | |
| Time of Sampling, HR | 1-2 | 5-6 | 23-24 | 1-2 | 5-6 | 23-24 |
| Component Wt % | | | | | | |
| Naph | 55.3 | 54.4 | 61.9 | 58.1 | 58.0 | 63.7 |
| 2-MIN | 24.0 | 23.1 | 18.0 | 21.9 | 20.6 | 17.8 |
| 1-MIN | 4.1 | 3.8 | 2.8 | 4.2 | 3.9 | 3.3 |
| 2,7-DIN | 1.3 | 1.6 | 1.3 | 1.1 | 1.1 | 0.9 |
| 2,6-DIN | 4.9 | 6.4 | 5.5 | 4.9 | 5.4 | 4.9 |
| Other DIN | 1.1 | 1.5 | 1.0 | 1.0 | 1.0 | 0.9 |
| TIN | 0 | 0 | 0 | 0 | 0 | 0 |
| Iodine | 2.9 | 3.5 | 7.3 | 5.0 | 6.0 | 8.9 |
| EXAMPLE NO. | 3 | | | Average Ex 1-3 | | |
| Time of Sampling, HR | 1-2 | 5-6 | 23-24 | 1-2 | 5-6 | 23-24 |
| Component Wt % | | | | | | |
| Naph | 60.7 | 58.9 | 58.0 | 58.0 | 57.1 | 61.2 |
| 2-MIN | 21.8 | 19.4 | 17.1 | 22.6 | 21.0 | 17.6 |
| 1-MIN | 3.7 | 3.2 | 2.7 | 4.0 | 3.6 | 2.9 |
| 2,7-DIN | 1.2 | 1.4 | 1.2 | 1.2 | 1.4 | 1.1 |
| 2,6-DIN | 4.8 | 6.0 | 5.5 | 4.9 | 5.9 | 5.3 |
| Other DIN | 1.0 | 1.3 | 1.2 | 1.0 | 1.3 | 1.0 |
| TIN | 0 | 0.2 | 0.2 | 0 | 0.1 | 0.1 |

TABLE 1-continued

PERFORMANCE OF FRESH CATALYST

| Iodine | 4.2 | 5.4 | 7.1 | 4.0 | 5.0 | 7.8 |

KEY:
Naph = naphthalene
2-MIN = 2-iodonaphthalene
1-MIN = 1-iodonaphthalene
2,7-DIN = 2,7-diiodonaphthalene
2,6-DIN = 2,6-diiodonaphthalene
Other DIN = all other isomers of diiodonaphthalene exclusive of the 2,7- and the 2,6- isomers
TIN = all isomers of triiodonaphthalene.

TABLE 2

PERFORMANCE OF REGENERATED CATALYST

| EXAMPLE NO. | 5 | | | 6 | | |
|---|---|---|---|---|---|---|
| Time of Sampling, HR | 1-2 | 5-6 | 23-24 | 1-2 | 5-6 | 23-24 |
| Component Wt % | | | | | | |
| Naph | 60.7 | 57.6 | 59.9 | 56.4 | 58.3 | 58.8 |
| 2-MIN | 23.7 | 22.2 | 21.2 | 23.6 | 21.8 | 19.4 |
| 1-MIN | 3.6 | 3.4 | 3.3 | 3.7 | 3.4 | 3.0 |
| 2,7-DIN | 1.6 | 1.5 | 1.2 | 1.5 | 1.4 | 1.1 |
| 2,6-DIN | 7.6 | 7.4 | 7.3 | 7.1 | 7.2 | 6.6 |
| Other DIN | 1.5 | 1.4 | 0.4 | 1.3 | 1.3 | 1.0 |
| TIN | 0.2 | 0.4 | 0 | 0 | 0 | 0.2 |
| Iodine | 3.5 | 4.1 | 4.9 | 2.7 | 3.6 | 5.0 |

| EXAMPLE NO. | Average Ex 5-6 | | |
|---|---|---|---|
| Time of Sampling, HR | 1-2 | 5-6 | 23-24 |
| Component Wt % | | | |
| Naph | 58.6 | 58.0 | 59.4 |
| 2-MIN | 23.7 | 22.0 | 20.3 |
| 1-MIN | 3.7 | 3.4 | 3.2 |
| 2,7-DIN | 1.6 | 1.5 | 1.2 |
| 2,6-DIN | 7.4 | 7.3 | 7.0 |
| Other DIN | 1.4 | 1.4 | 0.7 |
| TIN | 0.1 | 0.2 | 0.1 |
| Iodine | 3.1 | 3.9 | 5.0 |

KEY:
Naph = naphthalene
2-MIN = 2-iodonaphthalene
1-MIN = 1-iodonaphthalene
2,7-DIN = 2,7-diiodonaphthalene
2,6-DIN = 2,6-diiodonaphthalene
Other DIN = all other isomers of diiodonaphthalene exclusive of the 2,7- and the 2,6- isomers
TIN = all isomers of triiodonaphthalene.

TABLE 3

DIFFERENCES BETWEEN COMPONENT WEIGHT PERCENTAGES

| | EXAMPLES 1-6 | | |
|---|---|---|---|
| Time of Sampling, HR | 1-2 | 5-6 | 23-24 |
| Component Weight & Differences (Average EX 5-6)-(Average EX 1-3) | | | |
| Naph | 0.6 | 0.9 | −1.8 |
| 2-MIN | 1.1 | 1.0 | 2.7 |
| 1-MIN | −0.3 | −0.2 | 0.3 |
| 2,7-DIN | 0.4 | 0.1 | 0.1 |
| 2,6-DIN | 2.5 | 1.4 | 1.7 |
| Other DIN | 0.4 | 0.1 | −0.3 |
| TIN | 0.1 | 0.1 | 0 |
| Iodine | −0.9 | −1.1 | −2.8 |

KEY:
Naph = naphthalene
2-MIN = 2-iodonaphthalene
1-MIN = 1-iodonaphthalene
2,7-DIN = 2,7-diiodonaphthalene
2,6-DIN = 2,6-diiodonaphthalene
Other DIN = all other isomers of diiodonaphthalene exclusive of the 2,7- and the 2,6- isomers
TIN = all isomers of triiodonaphthalene.

What is claimed is:

1. A process comprising
   (A) reacting within a reaction zone naphthalene or benzene, a source of iodine and a source of molecular oxygen in the presence of a 13X zeolite which has greater than 10% of the exchangeable cations as alkali, alkaline earth or rare earth metals,
   (B) continuing the reaction until the activity of the zeolite is diminished,
   (C) discontinuing the delivery of the aromatic compound and iodine to the reaction zone,
   (D) regenerating the zeolite within a regeneration zone by
      (1) applying vacuum or delivering a source of molecular oxygen or inert gas at a temperature above 100° C. to remove a portion of the volatile compounds from the zeolite,
      (2) cooling the zeolite to a temperature below 100° C.,
      (3) contacting the zeolite with an aqueous solution having a pH in the range of 7 to 14,
      (4) drying the zeolite,
      (5) delivering an oxygen containing calcination gas and heating the zeolite to a temperature in the range of 350° to 450° C.,
      (6) cooling the zeolite to a temperature below 100° C.,
      (7) contacting the zeolite with an aqueous solution having a pH in the range of 7 to 14, and
   (E) resuming Step (A).

2. The process of claim 1 wherein the zeolite in steps (D)(3) and (D)(7) is contacted with an aqueous solution having a pH in the range of 9 to 14 and a temperature in the range of 0° C. to 100° C.

3. A process comprising
   (A) reacting within a reaction zone naphthalene, iodine and molecular oxygen in the presence of an 13X zeolite which has greater than 10% of the exchangeable cations as alkali, alkaline earth or rare earth metals,
   (B) Continuing the reaction until the activity of the zeolite is diminished,
   (C) discontinuing the delivery of naphthalene and iodine to the reaction zone,
   (D) regenerating the zeolite within a regeneration zone by
      (1) applying vacuum or delivering molecular oxygen or inert gas at a temperature above 100° C. to remove a portion of the volatile compounds from the zeolite,
      (2) cooling the zeolite to a temperature in the range of 20° C. to 80° C.,
      (3) contacting the zeolite with an aqueous solution having a pH in the range of 11 to 13.2 and a temperature in the range of 20° C. to 80° C.,
      (4) drying the zeolite at a temperature in the range of 80° C. to 120° C.,
      (5) delivering an oxygen containing calcination gas and heating the zeolite to a temperature in the range of 350° to 450° C.,
      (6) cooling the zeolite to a temperature in the range of 20° C. to 80° C.,
      (7) contacting the zeolite with an aqueous solution having a pH in the range of 11 to 13.2, and at a temperature in the range of 20° C. to 80° C.,
   (E) resuming Step (A).

* * * * *